United States Patent [19]

Brandes et al.

[11] 4,340,769

[45] Jul. 20, 1982

[54] PROCESS FOR THE CONTINUOUS PRODUCTION OF LOWER ALIPHATIC ALCOHOLS

[75] Inventors: Günter Brandes, Hamburg; Wilhelm Neier, Orsoy; Johannes Wöllner, Moers; Werner Webers, Orsoy, all of Fed. Rep. of Germany; Walter F. deVleesschauwer, Ghent, Belgium

[73] Assignee: Deutsche Texaco Aktiengesellschaft, Hamburg, Fed. Rep. of Germany

[21] Appl. No.: 945,764

[22] Filed: Sep. 25, 1978

Related U.S. Application Data

[63] Continuation of Ser. No. 790,204, Apr. 25, 1977, abandoned, which is a continuation-in-part of Ser. No. 593,396, Jul. 7, 1975, abandoned, which is a continuation of Ser. No. 377,662, Jul. 9, 1973, abandoned.

[30] Foreign Application Priority Data

Jul. 11, 1972 [DE] Fed. Rep. of Germany ........ 2233967

[51] Int. Cl.³ .............................................. C07C 29/04
[52] U.S. Cl. ................................................... 568/899
[58] Field of Search .......................................... 568/899

[56] References Cited

U.S. PATENT DOCUMENTS 2,813,908  11/1957  Young ................................. 260/614
3,793,379  2/1974  Rosscup et al. ..................... 568/899

FOREIGN PATENT DOCUMENTS 2147737  3/1973  Fed. Rep. of Germany ...... 568/899
2147739  4/1973  Fed. Rep. of Germany ...... 568/899

*Primary Examiner*—Joseph E. Evans
*Attorney, Agent, or Firm*—Carl G. Ries; Robert A. Kulason; James J. O'Loughlin

[57] ABSTRACT

A method is provided for the continuous production of saturated aliphatic alcohols having from 2 to 5 carbon atoms by hydrating the corresponding aliphatic olefin in the presence of a sulfonated styrene-divinylbenzene copolymer catalyst having a specific surface area measured in the dry state employing the BET method of:
  (a) less than 1 $m^2/g$ if the water-wet resin is dried, and
  (b) greater than 1 $m^2/g$ if the water is displaced from the water-wet resin by a slightly polar or a nonpolar organic solvent and the so dewatered resin is dried.

14 Claims, No Drawings

PROCESS FOR THE CONTINUOUS PRODUCTION OF LOWER ALIPHATIC ALCOHOLS

This is a continuation, of application Ser. No. 790,204, filed Apr. 25, 1977, now abandoned which is a continuation-in-part of application. Ser. No. 593,396, filed on July 7, 1975, now abandoned, which is a continuation of application Ser. No. 377,662 filed on July 9, 1973, now abandoned.

BACKGROUND OF THE INVENTION

1. Field of the Invention

Methods for the preparation of aliphatic alcohols having from 2 to 5 carbon atoms from the corresponding olefins are well known. Broadly, an enriched olefin feedstream is reacted in the presence of an acidic reacting catalyst at an elevated temperature to produce a reaction product containing either a saturated aliphatic alcohol or its ester which can be hydrolyzed to the alcohol. In earlier processes, sulfuric acid was employed as the preferred catalyst. This particular type of reaction resulted in the formation of an ester of the alcohol as an intermediate reaction product. The alcohol ester was then hydrolyzed to form the alcohol and a dilute aqueous solution of sulfuric acid. Serious drawbacks to this esterification process was the corrosivenesss of the sulfuric acid catalyst to process equipment and the large energy input required to return the sulfuric acid to a purity and a concentration that permitted its reuse in the process.

Next, processes for the direct hydration of an olefin with water to produce an alcohol were developed. Direct hydration involves contacting an olefin feed stream and water with a solid catalyst having acidic reaction sites. Examples of earlier solid catalysts for this reaction were sulfuric acid deposited on silica gel or clay, and reduced tungsten oxide. A major problem experienced with the early direct hydration processes was that they led to the production of substantial amounts of undesired olefin polymer and ether by-products. Another feature which led to serious problems was the necessity to employ a high reaction temperature. Under the high temperature reaction conditions, the solid catalysts had inadequate stability and possessed a short catalyst life.

There is another class of solid acidic reacting catalysts whose development arose out of chemical processes unrelated to the direct hydration process for olefins. These are the ion exchange resin catalysts. Ion exchange resins came into use for decationization and water purification. Applications for these catalysts broadened leading to their use in metal recovery processes and in food and pharmaceutical industry processes. The synthetic sulfonated ion exchange resins were then proposed as catalysts for the direct hydration of olefins to the corresponding alcohol.

The ion exchange resin catalysts can be defined as synthetic aryl resins possessing a hydrocarbon skeleton combined with strong mineral acid groups. They comprise the solid cross-linked polymers of vinyl aromatic compounds, such as styrene or vinyl polymers, divinyl benzene and other monoethylenically unsaturated compounds. These catalysts can be prepared in a number of ways. In the case of a polystyrene type resin, a mixture of styrene and divinyl benzene, in which the divinyl benzene may constitute from about 4 to 20% of the mixture, is polymerized at an elevated temperature preferably in the presence of a catalyst to produce a solid polymeric resin. The product resin is conveniently produced in the form of a sphere. The resin is contacted with a free acid, such as sulfonic acid or sulfuric acid, and this reaction is conducted until many or all of the available reaction sites in the resin have taken on a sulfonic acid group. The general method for preparing the acid reacting ion exchange resin catalyst is well known and is not part of the present invention.

Since the ion exchange resins catalysts are totally synthetic materials, considerable latitude exists for their manufacture. Thus, a manufacturer may employ a number of olefinic monomers and utilize them in a broad range of proportions in the polymerization step leading to the linking or cross-linking structure of the resin. In addition, the actual polymerization of the olefin monomers is greatly influenced by the resin polymerization catalyst employed and by the conditions of polymerization including the temperature and duration of the reaction and the use of a solvent or emulsion for effecting the polymerization. Because of the number of variables involved in effecting the preparation of the catalyst, a broad range of ion exchange resin catalysts have been produced exhibiting markedly different physical structures and physical properties.

The physical structure of the ion exchange resin is a vital characteristic of the resin and has a material effect on the usefulness of this class of catalyst. The physical structure of the catalyst not only determines the amount of surface area that is available for effecting chemical reaction but also has a pronounced effect on the stability and the effective life of the catalyst.

Ion exchange resin catalysts are known to be subject to swelling in the presence of solvents. Thus, organic solvents such as benzene, toluene, xylene, carbon tetrachloride and trichloroethylene promote swelling and materially alter the physical structure of the ion exchange resin. Young, U.S. Pat. No. 3,813,908, teaches that granulated styrene-divinyl benzene hydrocarbon copolymers can be swelled by contact with 10 to 50 volume percent of tetrachloroethylene to as much as about 170% of the original copolymer volume. He also discloses that this swelling influences the subsequent disintegration characteristics of the polymer and that the use of a careful or moderate swelling technique can be effective for reducing catalyst disintegration or instability.

The management of the swelling characteristics of the ion exchange resin is also very important during the sulfonation reaction when the active acid groups are added to the available cites in the resin. The art teaches that a too rapid dilution of the resin with water tends to weaken the resin structure and can result in subsequent fracture of the catalyst granules.

Because the resin structure is fragile, it is essential to maintain a high water content in the catalyst during storage and until its introduction into a conversion process. Any undue loss of water content during this period can reduce the catalytic activity of the resin as well as its physical strength thereby leading to early disintegration of the granules upon subsequent contact with water. When a partially dried out resin is placed in water, the water absorption may be so rapid that severe disintegration of the granules takes place. This Young teaching points to the destabilizing elements that are factors in the manufacture, storage and in the handling of ion exchange resin catalysts. These destabilizing features, which are in addition to the substantial differences in the structures of the catalysts, further complicates the problem of selecting the most stable, long-lived catalyst for an olefin hydration process.

Work has been conducted to distinguish or classify the ion exchange resin catalysts according to their physical structure. Thus, certain of the ion exchange resin catalysts have been described as having a gel-type or microporous resin structure. Commercial ion exchange resin catalysts which have been disclosed as having a gel type structure include: Amberlite 120, Amberlite 124 and Dowex 50X8. Another class of ion exchange resin catalysts have been described in the technical and commercial literature as having a macroporous resin structure. Examples of macroporous ion exchange resins include Amberlyst No. 15, Amberlite 200 and Lewatit SPC 118/H. Members of both of these classes of ion exchange resins have been disclosed as useful in the olefin hydration process for alcohol production.

The classification work on ion exchange resin catalysts up to the present time is limited in extent. In general, the published physical characteristics of the resins have been determined under a single set of test conditions. Structural measurements taken under one set of conditions, however, are incapable of gauging the range of characteristics and structural changes in a resin that are brought about by swelling of the catalyst. As pointed out, this swelling is an inherent property of ion exchange resins and its occurrence exerts a vital influence on the effectiveness and the stability or catalyst life of the resin. The paucity of available physical characteristics on ion exchange resins under different conditions of swell or expansion and the absence of any known criteria on which to determine the ion exchange resin catalysts having the greatest stability and a remarkable ability to retain the sulfonic acid catalyst function leaves the art without any rule on how to select a superior catalyst for an olefin hydration process.

2. Description of the Prior Art

German Patent Application No. 1 210 768 discloses a process for the continuous preparation of isopropanol and diisopropyl ether by the catalytic hydration of propylene. The catalyst employed is a strongly acidic cation exchange resin consisting of a styrene polymer cross-linked with from about 5 to 20 weight percent of divinyl benzene containing approximately one sulfonic acid group per aromatic ring. The reaction conditions employed to produce alcohol as the main product include a pressure ranging between 17 and 105 atmospheres, a temperature ranging from about 135° to 157° C. and a mole ratio of from 4 to 10 moles of water per mole of propylene. The feed rates for this process range from 0.5 to 10 volumes of liquid propylene per volume of wet catalyst per hour which corresponds to about 6.7 to 123.4 moles of propylene per liter of catalyst per hour. This process provides a per pass conversion of from 20 to 90 moles of charged propylene with a conversion of about 35 percent being preferred. Under these conditions the optimum selectivity for isopropanol was reached at a temperature of 135° C., amounting to 69 mole percent of the propylene charge of which 22 mole percent were converted, the balance being by-products, namely 28 moles percent diisopropyl ether and 3 mole percent of propylene polymers.

U.S. Pat. No. 2,813,908 discloses a process in which the catalyst employed in a sulfonated copolymer consisting of about 88 to 96 percent styrene and from 12 to 4 percent of p-divinylbenzene, and containing from 12 to 16 weight percent of sulfur in the form of sulfonic acid groups. This patent discloses reaction temperatures from 120° to 220° C. a feed rate of from 0.5 to 1.5 volumes of liquid olefin per volume of catalyst per hour and a water to olefin mole ratio ranging from 0.3 to 1.5. This reference also shows that good selectivity for isopropyl alcohol is achieved at a low temperature, i.e., about 120° C., and at a low conversion of about 3.9 mole percent. When a higher temperature (170° C.) was employed the conversion of propylene rose to about 35 mole percent but this was accompanied by the selectivity for isopropyl alcohol dropping to 55 percent, and with a high production, about 45 percent, of diisopropyl ether.

German Patent Application No. 1 291 729 which discloses a processes employing a strongly acidic ion exchange resin as catalyst, teaches that these catalysts have a relatively short effective life time due to the hydrolysis of the aromatic bonded sulfonic acid groups, particularly at higher temperatures. The catalyst life generally is no longer than a few hundred on-stream hours. This reference discloses a way to prolong the catalyst life considerably by using exchange resins with aliphatic or non-aromatic bonded sulfonic acid groups. However, these resins have not been available commercially because their preparation is so complicated.

Another known method of mitigating the drawbacks of the prior art processes for the catalytic hydration of lower olefins with strongly acidic ion exchange resins in a trickle type reactor is by varying the operating conditions and using a different type of resin with aromatic bonded sulfonic acid groups. The journal "Industrial and Engineering Chemistry", Product Research and Development, Vol. 1 (1962), No. 4, pp. 296–302, published a paper which, in addition to showing the influence of pressure, temperature, throughput and other parameters upon IPA yield, selectivity, and space-time yield compares two commercial catalyst, i.e. "Amberlite IR-120" and "Amberlyst 15", of which the latter has a macroreticular structure and a particularly large specific surface area. The properties of these two synthetic resins are compared to each other in the "Journal of Polymer Science", Part C, 1967, pp. 1457–69, on page 1463. According to this paper, "IR-120" is of the gel type, has a specific surface area below 0.1 m²/g, a pore radius which can hardly be measured, a porosity of 0.003 ml/ml resin, a water absorption capacity of 46 weight percent, and an ion exchange total capacity of 4.6 milliequivalents/g.

"Amberlyst 15" is a macroporous resin, has a specific surface area of 54,8 m²/g, an average pore diameter of 288 Å, a porosity of 0.367/ ml/ml resin, a water absorption capacity of 49 weight percent, and an ion exchange total capacity of 4.8 milliequivalents/g.

Although the two exchange resins differ quite considerably structurally, their performance in the hydration of propylene are reported to be rather similar as far as resistance of hydrolysis and catalyst performance are concerned (cf. the aforementioned paper "Ind. Eng. Chem.", page 297).

SUMMARY OF THE INVENTION

The process of this invention provides an improvement in the direct hydration of an aliphatic olefin having from to 2 to 5 carbon atoms to the corresponding lower saturated aliphatic alcohol by contacting a feed stream of said olefin and water with a particular highly acidic sulfonated styrene-divinylbenzene copolymer catalyst preferably in a fixed bed reactor. More specifically, the present process involves the direct hydration of the prescribed aliphatic olefins in a reaction with water employing a sulfonated styrene-divinylbenzene copolymer which has a specific surface area, measured in the dry state using the BET method, of (a) less than 1 m$^2$/g, when the water-wetted copolymer is dried, and
(b) greater than 1 m$^2$/g, preferably greater than 2 m$^2$/g, when the water is displaced from the water-wetted resin by a slightly polar or a nonpolar organic solvent, and the resin thus dewatered is then dried.

The catalyst employed in this reaction comes within a broad class of synthetic aryl cation exchange resins generally employed in a highly acid form containing sulfonic acid groups. The hydrocarbon skeleton consists of a copolymer of styrene and divinylbenzene. In general, the hydrocarbon skeleton consists of from about 80 to 95 percent styrene and from about 20 to 5 percent divinylbenzene with the preferred range for the divinylbenzene being from 10 to 20 percent. This is treated with a sulfur-containing acid until it becomes highly acidic with sulfonic acid groups. In general, this class of catalyst will contain from about 0.2 to 1 sulfonic acid groups per aromatic ring in the cation exchange resin.

It has been found that the process of the invention for the continuous production of lower alcohols can be conducted with surprising and unexpected effectiveness by employing as the catalyst a cation exchange resin of the sulfonated styrene-divinylbenzene copolymer type with certain critical specific surface areas and/or pore volumes within specific ranges. The specific surface areas and pore volumes of the catalyst are determined in a simple manner after the following pretreating steps:

Method I (1) 20 grams of the cation exchange resin is suspended in 150 ml of distilled water at ambient temperature and stirred several times. Thereafter, the resin is allowed to settle and the supernatant water decanted.
(2) Step (1) was repeated with 200 ml of distilled water.
(3) By means of a Buechner funnel the water-wetted resin is freed of adherent water, followed by applying vacuum for 10 minutes.
(4) The predried resin is vacuum dried in a porcelain dish for about 12 hours at a temperature of about 80° C.

Method II (1) 30 grams of the cation exchange resin is pretreated according to Method I, steps (1) to (3);
(2) it is then transferred to a glass tube having an inside diameter of 2.54 cm, closed at the bottom with a coarse fritted glass support, and successively eluated with 500 ml of pure methanol,
(3) 500 ml of pure benzene, and, finally,
(4) 500 ml of pure isooctane; then,
(5) it is transferred to a porcelain dish to be vacuum dried for about 12 hours at a temperature of 80° C.

After the resin samples have been so pretreated, their specific surface area(s) are measured using the BET method (cf. JACS 60 (1938), pp. 309–319 and 59 (1937), pp. 1-53-1564 and 2682-2689). The pore volume of the samples is determined as the difference between grain and skeletal volumes, using the well known Hg/H$_2$O penetration method. By grain volume is meant the volume of mercury displaced by 1 g of the resin sample; by skeletal volume the amount of water displaced by the aforesaid amount of the resin sample.

Tests have shown that gel type resins have a specific surface areas of $<1$ m$^2$/g, as determined according to both Method I and Method II. Typical macroporous resins have specific surface areas $s_I>1$ m$^2$/g, and $s_{II}>1$ m$^2$/g as determined by Methods I and II.

The resins employed for performing the process of the invention have a specific surface area $s_I<1$ m$^2$/g with Method I and $s_{II}>1$ m$^2$/g, preferably $s_{II}>2$ m$^2$/g with Method II.

When pretreated according to Methods I and II above resins can also be classified by their pore volume. Thus, the pore volume $v_I$ and $v_{II}$ of $<0.10$ ml/g resin, respectively, characterize gel type resins, and pore volumes $v_I$ and $v_{II}$ of $>0.10$ ml/g characterize or are typical for macroporous resins, while pore volume $v_I$ of $<0.10$ ml/g and $v_{II}$ of $>0.10$ ml/g characterize the resins employed in the process of the invention.

The catalysts employed in the process of this invention lie in a critical range between the gel type and the typical macroporous resins with respect to their specific surface area and their pore volume. A particular feature of the resins claimed for the process of the invention is that drying of the wet resins effects a contraction of their matrix so that their "internal" porosity only is reduced. This internal porosity, however, can be maintained if the water is displaced from the resin by solvents of diminishing polarity as described in Method II above. This unique property is believed to be responsible for the unexpectedly high catalytic activity of the resins claimed for the process of the invention. In other words, the outstanding results obtained from the instant process is due to the discovery of a specific type of resin within the broad class of sulfonated styrene-divinylbenzene copolymer resins which exhibits surprising catalyst stability and unexpectedly high retention of the sulfonic acid function in the catalyst.

The specific surface areas and pore volumes of the cation exchange resin catalysts employed herein following the test procedures described above are set forth in Table I below. Group A comprises three commercial catalysts having a macroporous pore structure. Group B comprises three commercial catalysts having a microporous pore structure. The catalysts in Group C represent a distinct group having newly discovered physical properties not possessed by the catalysts of Groups A & B.

TABLE I

| | | RESIN CATALYSTS | | | | |
| | | Specific Surface Area m$^2$g | | Pore Volume, ml/g | | |
| Group | Trade Name | Method I | Method II | Method I | Method II | Pore structure |
| | Amberlite 252[(1)] | below 1.0 | 39 | 0.074 | 0.183 | mesoporous |
| Group C | Relite CFS[(2)] | below 1.0 | 3.5 | 0.085 | 0.182 | " |
| | Lewatit SPC-108[(3)] | below 1.0 | 34 | 0.066 | 0.423 | " |
| | Amberlite 200[(1)] | 44 | 50.9 | 0.423 | 0.468 | macroporous |

TABLE I-continued
RESIN CATALYSTS

| Group | Trade Name | Specific Surface Area m²g | | Pore Volume, ml/g | | Pore structure |
| --- | --- | --- | --- | --- | --- | --- |
| | | Method I | Method II | Method I | Method II | |
| Group A | Amberlyst 15[(1)] | 41 | 57 | 0.39 | 0.45 | " |
| | Lewatit SPC-118[(3)] | 37 | 45.8 | 0.641 | 0.737 | " |
| | Amberlite IR 124[(1)] | below 0.1 | far below 1.0 | 0.063 | below 0.1 | microporous |
| Group B | Amberlite IR 120[(1)] | below 0.1 | far below 1.0 | below 0.1 | below 0.1 | " |
| | Dowex 50WX 12[(4)] | below 0.1 | far below 1.0 | below 0.1 | below 0.1 | " |

[(1)]Trade Mark of the Rohn & Haas Co.
[(2)]Trade Mark of Resindion - Div. of Sybron Corporation
[(3)]Trade Mark of Bayer
[(4)]Trade Mark of Dow Chemical Corp.

The olefinic hydrocarbons which are directly hydrated to alcohols according to this process are the $C_2$ to $C_5$ aliphatic olefins. Specific members include ethene, propene, butene-1, butene-2 and the pentenes, the normal or straight chain olefins being preferred. The preferred olefins for treatment by this process are propene, butene-1 and butene-2.

Since the olefins are not easily obtained in a highly purified state, the olefin component of the feed mixture will generally contain some saturated aliphatic hydrocarbons. Thus, typical olefin components employed in the water-olefin feed mixture include a propene-propane stream, a butene-1 butane stream or similar mixtures. In general, the olefin component of the feed mixture should consist of at least about 75 percent of the olefin to be reacted with a preferred stream consisting of at least 85 to 90 percent or more of the olefin reactant.

The olefin component is employed with water to provide a water-olefin feed mixture. The amount of water employed in the feed mixture in this process is very important. The feed mixture must consist of at least 1 up to 30 moles of water per mole of olefin. A preferred ratio in this regard is from about 10 to 20 moles of water per mole of olefin with a particularly preferred ratio being from about 15 to 20 moles of water per mole of olefin.

The process is conducted in a fixed-bed, tower-like or trickle-type reaction column. The reactor is a closed vessel suitable for containing the liquid-gaseous reactants under the essential temperatures and pressures. A solid catalyst is disposed within the reactor on one or more fixed beds. In addition to an inlet at the head of the reactor for the water-olefin feed mixture, the reaction vessel may have one or more auxiliary inlet lines for process feed water disposed downstream in the reactor from the water-olefin inlet.

The reactor is highly effective with a cross-sectional load of the reactor tube of from about 1-40, preferably about 5-25 moles of water per cm² of tubular cross-sectional area per hour.

The temperature and pressure employed in this process are critical. Broadly, the reaction temperature for this process is from 120° to 180° C. An initial inlet reaction temperature for the water-olefin feed mixture of from about 120° to 165° C. is usually employed with the preferred inlet temperature range being from about 135° to 155° C.

This reaction is generally effected at a pressure ranging from about 60 to 200 atmospheres. A preferred operating pressure, however, is from about 80 to about 125 atmospheres.

The experimental examples including the comparison examples and the examples illustrating the process of the invention were conducted under identical operating conditions. The olefin feed was a $C_3$ mixture consisting of 92 percent by volume of propylene. The reactor employed was a trickle type tubular reactor having an inside diameter of 26 millimeters and a height of 3 meters (3000 mm). The reactor was maintained at a constant temperature of 135° C. and a pressure of 100 bar.

The runs were conducted by charging the reactor at the top with 1000 grams of water and 122 grams of the above-described $C_3$ mixture per liter of catalyst per hour. The runs were continued for a period of 2000 hours. At every 200 hour interval tests were conducted to follow the course of the process. The percent propylene conversion basis the propylene feed as well as the moles of isopropyl alcohol produced per liter of catalyst per hour are given for each interval.

The condition or stability of the catalyst was determined by testing for the sulfonic acid content of the resin. This was reported as the percent sulfonic acid loss at each 200 hour interval of the run.

The results are given in the following examples:

EXAMPLE I

| | MACROPOROUS RESIN CATALYSTS | | |
| --- | --- | --- | --- |
| Test Period Hrs. | Catalyst performance Mol IPA 1 catalyst/hr | Propylene Conversion % | Sulfonic Acid Loss % |
| Run 1 - Amberlite 200 | | | |
| 200 | 1,91 | 71,47 | 16,0 |
| 400 | 1,88 | 70,35 | 25,9 |
| 600 | 1,81 | 67,73 | 30,8 |
| 800 | 1,76 | 65,86 | 37,0 |
| 1000 | 1,70 | 63,61 | 42,4 |
| 1200 | 1,65 | 61,74 | 45,1 |
| 1400 | 1,58 | 59,91 | 47,6 |
| 1600 | 1,44 | 53,88 | 51,0 |
| 1800 | 1,32 | 47,39 | 54,1 |
| 2000 | 1,14 | 42,66 | 56,3 |
| Run 2 - Amberlyst 15 | | | |
| 200 | 1,82 | 68,10 | 18,5 |
| 400 | 1,76 | 65,86 | 26,3 |
| 600 | 1,68 | 62,86 | 31,9 |
| 800 | 1,60 | 59,87 | 38,4 |
| 1000 | 1,54 | 57,63 | 43,0 |
| 1200 | 1,46 | 54,63 | 46,0 |
| 1400 | 1,40 | 52,39 | 48,1 |
| 1600 | 1,33 | 49,77 | 51,9 |
| 1800 | 1,20 | 44,90 | 55,6 |
| 2000 | 1,10 | 41,16 | 58,3 |
| Run 3 - Lewatit SPC 118 | | | |
| 200 | 2,10 | 78,58 | 15,7 |
| 400 | 1,98 | 74,09 | 23,4 |
| 600 | 1,90 | 71,09 | 31,8 |
| 800 | 1,83 | 68,48 | 36,2 |
| 1000 | 1,72 | 64,36 | 40,2 |

MACROPOROUS RESIN CATALYSTS -continued

| Test Period Hrs. | Catalyst performance Mol IPA 1 catalyst/hr | Propylene Conversion % | Sulfonic Acid Loss % |
|---|---|---|---|
| 1200 | 1,68 | 62,86 | 44,0 |
| 1400 | 1,64 | 61,37 | 46,7 |
| 1600 | 1,60 | 59,87 | 48,9 |
| 1800 | 1,55 | 58,00 | 51,3 |
| 2000 | 1,50 | 56,13 | 53,1 |

At the end of the 2000 hour test runs for Runs 1 to 3, the average percent sulfonic acid loss for the three prescribed macroporous resin catalysts was 55.9 percent.

EXAMPLE II

MACROPOROUS RESIN CATATYSTS

| Test Period Hrs. | Catalyst performance Mol IPA 1 catalyst/hr | Propylene Conversion % | Sulfonic Acid Loss % |
|---|---|---|---|
| Run 4 - Amberlite-IR 124 | | | |
| 200 | 1,91 | 71,47 | 12,6 |
| 400 | 1,89 | 70,72 | 18,9 |
| 600 | 1,86 | 69,60 | 24,1 |
| 800 | 1,84 | 68,85 | 29,2 |
| 1000 | 1,84 | 68,85 | 32,5 |
| 1200 | 1,80 | 67,35 | 35,0 |
| 1400 | 1,74 | 65,11 | 36,9 |
| 1600 | 1,66 | 62,12 | 38,5 |
| 1800 | 1,54 | 57,62 | 40,2 |
| 2000 | 1,46 | 54,63 | 41,7 |
| Run 5 - Amberlite IR-120 | | | |
| 200 | 1,76 | 65,86 | 13,5 |
| 400 | 1,72 | 64,36 | 19,8 |
| 600 | 1,70 | 63,61 | 25,1 |
| 800 | 1,69 | 63,24 | 30,0 |
| 1000 | 1,68 | 62,86 | 33,8 |
| 1200 | 1,66 | 62,11 | 36,5 |
| 1400 | 1,60 | 59,87 | 38,4 |
| 1600 | 1,54 | 57,62 | 40,6 |
| 1800 | 1,48 | 55,38 | 42,1 |
| 2000 | 1,40 | 52,39 | 43,6 |
| Run 6 - Dowex 50 WX 12 | | | |
| 200 | 1,77 | 66,23 | 14,2 |
| 400 | 1,75 | 65,48 | 20,1 |
| 600 | 1,68 | 62,86 | 25,6 |
| 800 | 1,66 | 62,12 | 30,4 |
| 1000 | 1,63 | 60,99 | 34,1 |
| 1200 | 1,60 | 59,87 | 36,8 |
| 1400 | 1,55 | 58,00 | 39,0 |
| 1600 | 1,52 | 56,88 | 41,1 |
| 1800 | 1,45 | 54,26 | 42,9 |
| 2000 | 1,41 | 52,76 | 44,3 |

At the end of the 2000 hour test runs for Runs 4 to 6, the average percent sulfonic acid for the three prescribed microporous resin catalysts was 43.2 percent.

EXAMPLE III

MESOPOROUS RESIN CATALYST

| | | | |
|---|---|---|---|
| Run 7 - Amberlite 252 | | | |
| 200 | 2,04 | 76,33 | 7,8 |
| 400 | 1,99 | 74,46 | 11,8 |
| 600 | 1,96 | 73,34 | 15,4 |
| 800 | 1,93 | 72,22 | 18,2 |
| 1000 | 1,89 | 70,72 | 20,8 |
| 1200 | 1,85 | 69,23 | 22,6 |
| 1400 | 1,82 | 68,10 | 24,3 |
| 1600 | 1,77 | 66,23 | 26,0 |
| 1800 | 1,73 | 64,74 | 27,6 |
| 2000 | 1,68 | 62,86 | 29,3 |

| Test Period Hrs. | Catalyst performance Mol. IPA 1 catalyst/hr | Propylene Conversion % | Sulfonic Acid Loss % |
|---|---|---|---|
| Run 8 - Relite CFS | | | |
| 200 | 2,12 | 79,33 | 6,4 |
| 400 | 2,04 | 76,33 | 9,6 |
| 600 | 1,98 | 74,09 | 12,6 |
| 800 | 1,96 | 73,34 | 15,5 |
| 1000 | 1,95 | 72,97 | 18,3 |
| 1200 | 1,92 | 71,84 | 20,7 |
| 1400 | 1,89 | 70,72 | 22,6 |
| 1600 | 1,86 | 69,60 | 24,3 |
| 1800 | 1,82 | 68,10 | 26,0 |
| 2000 | 1,76 | 65,86 | 27,5 |
| Run 9 - Lewatit SPC-108 | | | |
| 200 | 2,01 | 75,21 | 8,1 |
| 400 | 2,00 | 74,84 | 12,0 |
| 600 | 1,94 | 72,59 | 15,8 |
| 800 | 1,90 | 71,09 | 19,4 |
| 1000 | 1,87 | 69,97 | 22,2 |
| 1200 | 1,87 | 69,97 | 24,0 |
| 1400 | 1,85 | 69,22 | 25,5 |
| 1600 | 1,79 | 66,98 | 26,9 |
| 1800 | 1,71 | 63,98 | 28,4 |
| 2000 | 1,65 | 61,74 | 30,0 |

At the end of the 2000 hour test runs for Runs 7 to 9, the average percent sulfonic acid loss for the three prescribed mesoporous resin catalysts was 28.9 percent.

The foregoing examples show the improvement in the stability and in the high retention of the sulfonic acid function of the prescribed cation exchange resin catalysts in the process of the present invention. This is particularly well illustrated by the condition of the cation exchange resin catalyst i.e., the sulfonic acid content, after the catalyst had been used to effect the continuous hydration of propylene for 2000 hours.

Thus, in Example I (Runs 1-3) the three macroporous resin catalysts lost an average of 55.9 percent of the sulfonic acid groups originally present in the macroporous resin catalyst.

Example II (Runs 4-6) the three microporous resin catalysts lost an average of 43.2 percent of the sulfonic acid groups originally present in the resin catalyst.

The stability of the sulfonic acid function in the process of the invention, illustrated by Runs 7-9 of Example III, sharply contrasts with the performance of the prior art processes. In the process of the invention, the average percent sulfonic acid loss in the prescribed catalyst was only 28.9 percent. This surprising result establishes that an unexpected advance in the direct hydration process for olefins has been achieved by the present invention. The magnitude of this improvement is also shown by the substantially higher yield of isopropyl alcohol being continuously produced by the process of the invention at the 2000 hour run duration time in the process.

In other tests, the process of the invention has been shown to be capable of continuous extended process runs of 8000 hours duration or longer. This capability is a direct result of the discovery of a highly stable and durable catalyst with its unusual ability to retain the sulfonic acid active groups in the process. The prior art processes which employ catalysts exhibiting a relatively high loss of sulfonic acid active groups become totally inactive in substantially shorter run periods.

We claim:

1. In a process for preparing a saturated aliphatic alcohol having from 2 to 5 carbon atoms in a closed fixedbed reactor containing a sulfonated synthetic aryl cation exchange resin catalyst by reacting a water-olefin feed mixture in which said olefin component consists of at least 75 mole percent of a $C_2$ to $C_5$ aliphatic olefin and said water-olefin feed mixture consists of from about 1. to 40 moles of water per mole of said olefin, under hydration conditions at a temperature from about 120° to 180° C. and a pressure ranging from about 60 to 200 atmospheres gauge to recover an effluent reaction mixture rich in said saturated aliphatic alcohol, the improvement which comprises employing a sulfonated styrene-divinylbenzene copolymer cation exchange resin catalyst having a specific surface area measured in the dry state employing the BET method, of:
    (a) less than 1 $m^2/g$, when the water-wet resin in dried, and
    (b) greater than 1 $m^2/g$, when the water is displaced from the water-wet resin by a slightly polar or a non-polar organic solvent and the dewatered resin then dried.

2. A process according to claim 1, in which said catalyst has a specific surface area of less than about 1 $m^2/g$ when it is digested with excess water, freed of the excess water by filtration and vacuumed dried at about 80° C. and which has a specific surface area of greater than about 1 $m^2/g$ when, subsequent to the treatment with water, said water is displaced first by a lower aliphatic alcohol, followed by treatment with an aromatic hydrocarbon and finally by treatment with an aliphatic hydrocarbon and then vacuumed dried at 80° C.

3. A process according to claim 1, in which said water is displaced in successive treatment with methanol, benzene and isooctane.

4. A process according to claim 1, in which said catalyst has a pore volume of less than about 0.1 ml/g when the water-wet resin is dried, and which has a pore volume of greater than about 0.1 ml/g when the water in said water-wet resin is displaced by a slightly polar or a non-polar organic solvent and then dewatered and dried.

5. A process according to claim 1, in which said styrene-divinylbenzene copolymer catalyst consists of from 80 to 95 percent styrene and from 20 to 5 percent divinylbenzene.

6. A process according to claim 1, in which said ion exchange resin catalyst copolymer consists of from 80 to 90 percent styrene and from 10 to 20 percent divinylbenzene.

7. A process according to claim 1, in which the specific surface area of the catalyst is greater than 2 $m^2/g$ when the water is displaced from the water-wet resin by a slightly polar or a non-polar organic solvent and the dewatered resin then dried.

8. A process according to claim 1, in which said drying is conducted in a vacuum at a temperature of 80° C. for 12 hours.

9. A process according to claim 1, in which said ion exchange resin catalyst contains from about 0.2 to 1 sulfonic acid groups per aromatic ring in the cation exchange resin.

10. In a process for preparing isopropyl alcohol in a closed fixed-bed reactor containing a sulfonated synthetic aryl cation exchange resin catalyst by reacting water-olefin feed mixture in which said olefin component consists of at least 75 mole percent of propylene and said water-olefin feed mixture consists of from about 1 to 40 moles of water per mole of said propylene, under hydration conditions at a temperature from about 120° to 180° C. and a pressure ranging from about 60 to 200 atmospheres gauge to recover an effluent reaction mixture rich in said isopropyl alcohol, the improvement which comprises employing a sulfonated styrene-divinylbenzene copolymer cation exchange resin catalyst having a specific surface area measured in the dry state employing the BET method, of:
    (a) less than 1 $m^2/g$, when the water-wet resin in dried, and
    (b) greater than 1 $m^2/g$, when the water is displaced from the water-wet resin by a slightly polar or a non-polar organic solvent and the dewatered resin then dried.

11. A process according to claim 10 in which said catalyst has a specific surface area of less than about 1 $m^2/g$ when it is digested with excess water, freed of the excess water by filtration and vacuumed dried at about 80° C. and which has a specific surface area of greater than about 1 $m^2/g$ when, subsequent to the treatment with water, said water is displaced first by a lower aliphatic alcohol, followed by treatment with an aromatic hydrocarbon and finally by treatment with an aliphatic hydrocarbon and then vacuumed dried at 80° C.

12. A process according to claim 10 in which the specific surface area of the catalyst is greater than 2 m/g when the water is displaced from the water-wet resin by a slightly polar or a non-polar organic solvent and the dewatered resin then dried.

13. A process according to claim 10 in which said water is displaced in successive treatment with methanol, benzene and isooctane.

14. A process according to claim 1 in which said catalyst has a pore volume of less than about 0.1 ml/g when the water-wet resin is dried, and which has a pore volume of greater than about 0.1 ml/g when the water in said water-wet resin is displaced by a slightly polar or a non-polar organic solvent and then dewatered and dried.

* * * * *